US011779282B2

(12) United States Patent
Chih et al.

(10) Patent No.: US 11,779,282 B2
(45) Date of Patent: Oct. 10, 2023

(54) METHOD FOR DETERMINING DEGREE OF RESPONSE TO PHYSICAL ACTIVITY

(71) Applicant: bOMDIC, Inc., New Taipei (TW)

(72) Inventors: Hao-Yi Chih, New Taipei (TW); Yu-Ting Liu, New Taipei (TW); Amy Pei-Ling Chiu, New Taipei (TW)

(73) Assignee: BOMDIC, INC., New Taipei (TW)

( * ) Notice: Subject to any disclaimer, the term of this patent is extended or adjusted under 35 U.S.C. 154(b) by 263 days.

(21) Appl. No.: 17/315,355

(22) Filed: May 10, 2021

(65) Prior Publication Data

US 2022/0354385 A1 Nov. 10, 2022

(51) Int. Cl.
| | |
|---|---|
| *A61B 5/00* | (2006.01) |
| *A61B 5/11* | (2006.01) |
| *A61B 5/024* | (2006.01) |
| *A61B 5/31* | (2021.01) |
| *A61B 5/389* | (2021.01) |
| *A61B 5/315* | (2021.01) |
| *G06N 3/045* | (2023.01) |
| *G06N 3/0464* | (2023.01) |

(52) U.S. Cl.
CPC ............ *A61B 5/7264* (2013.01); *A61B 5/024* (2013.01); *A61B 5/11* (2013.01); *A61B 5/31* (2021.01); *A61B 5/315* (2021.01); *A61B 5/389* (2021.01); *A61B 5/4812* (2013.01); *G06N 3/045* (2023.01); *G06N 3/0464* (2023.01)

(58) Field of Classification Search
CPC ......... A61B 5/7264; A61B 5/024; A61B 5/11; A61B 5/31; A61B 5/315; A61B 5/389; A61B 5/4812; A61B 5/02416; A61B 5/0245; A61B 5/02438; A61B 5/0816; A61B 5/369; A61B 5/398; A61B 5/02405; A61B 5/7267; G06N 3/045; G06N 3/0464
See application file for complete search history.

(56) References Cited

U.S. PATENT DOCUMENTS

| | | | |
|---|---|---|---|
| 10,076,273 B2 * | 9/2018 | Berckmans | A61B 5/165 |
| 11,195,118 B2 * | 12/2021 | Dibia | A61B 5/1118 |
| 2016/0081620 A1 * | 3/2016 | Narayanan | G01C 22/006 |
| | | | 600/595 |
| 2016/0086500 A1 * | 3/2016 | Kaleal, III | G09B 5/06 |
| | | | 434/257 |
| 2017/0215808 A1 * | 8/2017 | Shimoi | A61B 5/0205 |

(Continued)

OTHER PUBLICATIONS

Kim et al. (Unobtrusive Monitoring to Detect Depression for Elderly With Chronic Illnesses, IEEE, 2017) (Year: 2017).*

*Primary Examiner* — Mohammad K Islam
(74) *Attorney, Agent, or Firm* — Chieh-Mei Wang

(57) ABSTRACT

The present invention discloses a method for determining a degree of response to a physical activity. Acquire a physical activity signal measured by a sensing unit in the physical activity. Determine first data of a first physical activity feature set based on the physical activity signal. Determine a recognition of the degree of response to the physical activity based on the first data of the first physical activity feature set by a mathematical model describing a relationship between the first physical activity feature set and the degree of response to a physical activity. A portion of a first mechanism of the mathematical model adopts at least one portion of a second mechanism of a first neural network model associated with the second physical activity feature set.

25 Claims, 6 Drawing Sheets

(56) References Cited

U.S. PATENT DOCUMENTS

| | | | |
|---|---|---|---|
| 2020/0054289 A1* | 2/2020 | Shimol | A61B 5/7253 |
| 2020/0093386 A1* | 3/2020 | Biswas | G16H 50/20 |
| 2020/0175415 A1* | 6/2020 | Zou | G06N 20/00 |
| 2021/0162261 A1* | 6/2021 | Neumann | G06N 7/01 |
| 2021/0279554 A1* | 9/2021 | Ibtehaz | A61B 5/7278 |
| 2022/0054039 A1* | 2/2022 | Rahman | A61B 5/08 |
| 2022/0122735 A1* | 4/2022 | Sherkat | G06N 3/04 |
| 2022/0249906 A1* | 8/2022 | Phillips | A63B 24/0062 |
| 2022/0323855 A1* | 10/2022 | Khare | A63F 13/216 |

* cited by examiner

METHOD FOR DETERMINING DEGREE OF RESPONSE TO PHYSICAL ACTIVITY

BACKGROUND OF THE INVENTION

1. Field of the Invention

The present invention relates to a method for monitoring the physical activity, and more particularly to a method for determining a degree of response to the physical activity performed by the person.

2. Description of Related Art

When performing a physical activity, the person doesn't usually accurately know the degree of response to the physical activity. For example, when taking exercise, the person doesn't usually accurately know that he is relaxed, tired or exhausted; even if the person thinks that he is tired, he may not usually accurately know that he is lightly tired, moderately tired or heavily tired. For example, when sleeping, the person doesn't usually accurately know that he sleeps lightly or deep; even if the person thinks that he sleeps deep, he may not usually accurately know whether it meets the criterion of the deep sleep. So, it is difficult for the person who doesn't know the sleep pattern or the sleep stage to improve sleep habits, sleep quality or health status. When the person doesn't accurately know the degree of response to the physical activity, the optimal suggestion of the physical activity may be not accurately provided for him.

Accordingly, the present invention proposes a method for determining for determining a degree of response to the physical activity performed by the person to overcome the above-mentioned disadvantages.

SUMMARY OF THE INVENTION

When a person performs a physical activity, the degree of response to the physical activity can be regarded as how much effort made by the person for the physical activity, how the physical activity affects the person or a feedback provided by the person during the physical activity for the stimulus. The present invention builds up a mathematical model for accurately determining a recognition of the degree of response to the physical activity performed by the person based on the measured data of the first physical activity feature set by the mathematical model describing a relationship between the first physical activity feature set and the degree of response to the physical activity. Substantially, the mathematical model has a first input mode and a second input mode for determining a recognition of the degree of response to the physical activity performed by the person. In the first input mode, the first physical activity feature set is used as the input layer of the mathematical model. In the second input mode, a portion of the first mechanism of the mathematical model adopts at least one portion of the second mechanism of another neural network model associated with the second physical activity feature set. The second input mode can be regards as a hidden input mode of the mathematical model where the second physical activity feature set can be a hidden input layer of the mathematical model. A portion of the first mechanism of the mathematical model may be disposed between the input layer of the mathematical model and the medium layer I of the mathematical model or between the medium layer II of the mathematical model and the medium layer III of the mathematical model.

Specifically, besides the first physical activity feature set generally used as the input layer of the mathematical model for determining the degree of response to the physical activity performed by a person, at least one portion of the second mechanism of another neural network model also becomes a portion of the first mechanism of the mathematical model. Because the first mechanism of the mathematical model further takes into account the neural network feature derived from the second physical activity feature set highly correlated with the degree of response to the physical activity performed by the person, at least one portion of the second mechanism of another neural network model becoming a portion of the first mechanism of the mathematical model can increase a precision of determining the degree of response to the physical activity performed by the person.

By the algorithm implemented in the computer of the present invention, the computer of the present invention performs operations described in claims or the following descriptions to building up a mathematical model to determining a degree of response to a physical activity performed by the person.

In one embodiment, the present invention discloses a method for determining a degree of response to a physical activity. The method comprises: acquiring a physical activity signal measured by at least one sensor in the physical activity; determining, by a processing unit, first data of a first physical activity feature set based on the physical activity signal; and determining, by the processing unit, a recognition of the degree of response to the physical activity based on the first data of the first physical activity feature set by a mathematical model describing a relationship between the first physical activity feature set and the degree of response to the physical activity; wherein the mathematical model comprises a first mechanism directing a first input layer of the mathematical model to a first output layer of the mathematical model, wherein the first physical activity feature set is used as the first input layer of the mathematical model and the degree of response to the physical activity is used as the first output layer of the mathematical model; wherein a first neural network model comprises a second mechanism directing a second input layer of the first neural network model to a second output layer of the first neural network model, wherein the first physical activity feature set is used as the second input layer of the first neural network model and a second physical activity feature set is used as the second output layer of the first neural network model; wherein a first portion of the first mechanism directs a first topmost layer of the first portion of the first mechanism to a first bottommost layer of the first portion of the first mechanism, and at least one second portion of the second mechanism directs a second topmost layer of the at least one second portion of the second mechanism to a second bottommost layer of the at least one second portion of the second mechanism, wherein the first bottommost layer of the first portion of the first mechanism is not used as the first output layer of the mathematical model; wherein the first portion of the first mechanism of the mathematical model adopts the at least one second portion of the second mechanism of the first neural network model with the first topmost layer being the second topmost layer and the first bottommost layer being the second bottommost layer.

In one embodiment, the present invention discloses a method for determining a degree of response to a physical activity. The method comprises: acquiring a first physical activity signal measured by a first sensing unit in the physical activity; determining, by a processing unit, first data of a first physical activity feature set based on the first physical activity signal; and determining, by the processing unit, a recognition of the degree of response to the physical activity based on the first data of the first physical activity feature set by a mathematical model describing a first relationship between the first physical activity feature set and the degree of response to the physical activity; wherein a portion of a first mechanism of the mathematical model adopts at least one portion of a second mechanism of a first neural network model associated with a second physical activity feature set.

In one embodiment, the present invention discloses a method for determining a degree of response to a physical activity. The method comprises: acquiring a physical activity signal measured by at least one sensor in the physical activity; determining, by a processing unit, first data of a first physical activity feature set based on the physical activity signal; and determining, by the processing unit, a recognition of the degree of response to the physical activity based on the first data of the first physical activity feature set by a mathematical model describing a relationship between the first physical activity feature set and the degree of response to the physical activity; wherein the mathematical model comprises a first mechanism directing a first input layer of the mathematical model to a first output layer of the mathematical model, wherein the first physical activity feature set is used as the first input layer of the mathematical model and the degree of response to the physical activity is used as the first output layer of the mathematical model, wherein the first physical activity feature set comprises at least one first feature element, wherein one of the at least one first feature element of the first physical activity feature set is a heart rate; wherein a first neural network model comprises a second mechanism directing a second input layer of the first neural network model to a second output layer of the first neural network model, wherein the first physical activity feature set is used as the second input layer of the first neural network model and a second physical activity feature set is used as the second output layer of the first neural network model, wherein the second physical activity feature set comprises at least one second feature element, wherein one of the at least one second feature element of the second physical activity feature set is a heart activity parameter determined based on at least one beat and at least one beat interval alternating with the at least one beat of a heart activity signal; wherein a first portion of the first mechanism directs a first topmost layer of the first portion of the first mechanism to a first bottommost layer of the first portion of the first mechanism, and at least one second portion of the second mechanism directs a second topmost layer of the at least one second portion of the second mechanism to a second bottommost layer of the at least one second portion of the second mechanism, wherein the first bottommost layer of the first portion of the first mechanism is not used as the first output layer of the mathematical model; wherein the first portion of the first mechanism of the mathematical model adopts the at least one second portion of the second mechanism of the first neural network model with the first topmost layer being the second topmost layer and the first bottommost layer being the second bottommost layer.

The detailed technology and above preferred embodiments implemented for the present invention are described in the following paragraphs accompanying the appended drawings for people skilled in the art to well appreciate the features of the claimed invention.

BRIEF DESCRIPTION OF THE DRAWINGS

The foregoing aspects and many of the accompanying advantages of this invention will become more readily appreciated as the same becomes better understood by reference to the following detailed description when taken in conjunction with the accompanying drawings, wherein.

DETAILED DESCRIPTION OF THE ILLUSTRATED EMBODIMENTS

The detailed explanation of the present invention is described as following. The described preferred embodiments are presented for purposes of illustrations and description and they are not intended to limit the scope of the present invention.

Figure 1:
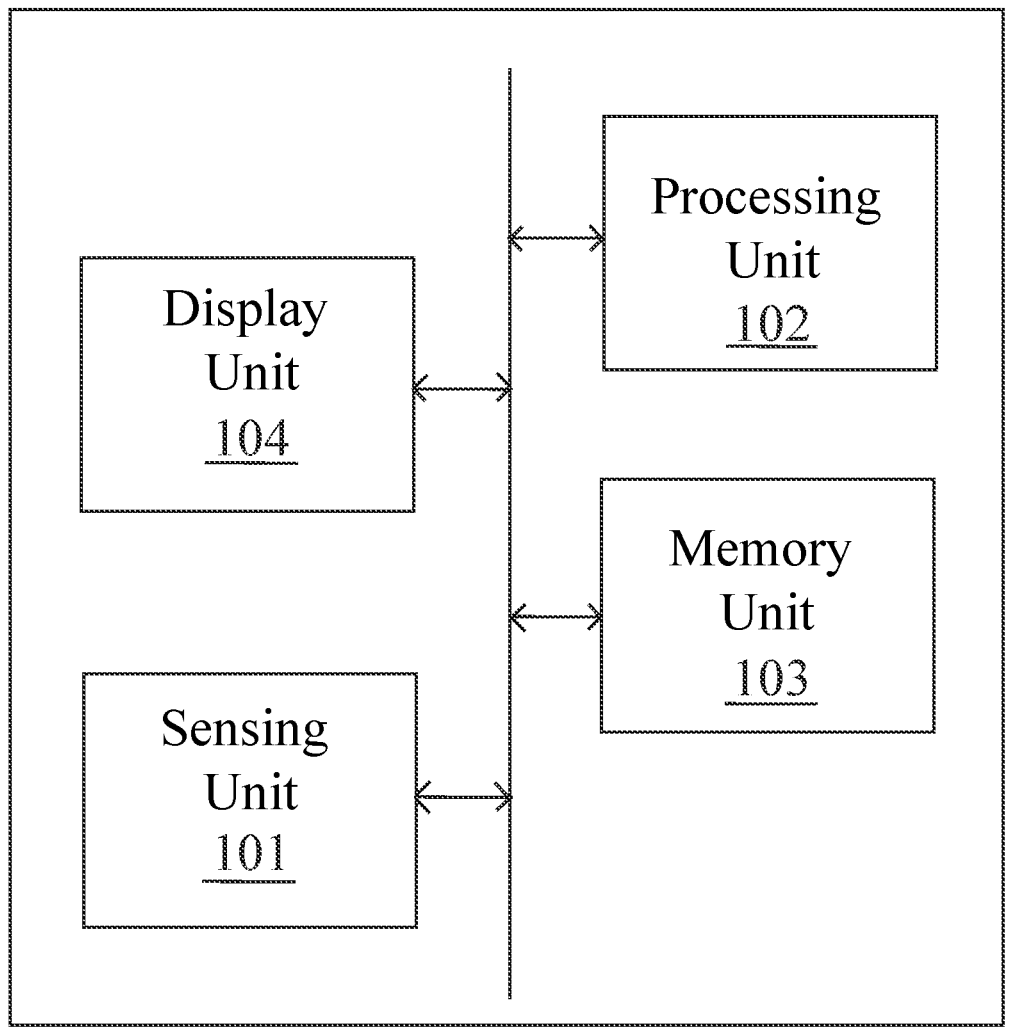
FIG. 1 illustrates a schematic block diagram of an exemplary apparatus in the present invention.

The method in the present invention may be applied in all kinds of apparatuses, such as a measurement system, the device worn on the individual (e.g., the device attached to the wrist belt or chest belt), a wrist top device, a mobile device, a portable device, a personal computer, a server or a combination thereof. FIG. 1 illustrates a schematic block diagram of an exemplary apparatus 100 in the present invention. The apparatus 100 may comprise a sensing unit 101 (e.g., at least one sensor), a processing unit 102, a memory unit 103 and a displaying unit 104. One unit may communicate with another unit in a wired or wireless way. The apparatus 100 may comprise at least one device; the sensing unit 101 may be in one device (e.g., the device worn on the individual or watch) and the processing unit 102 may be in another device (e.g., mobile device or mobile phone); the sensing unit 101 and the processing unit 102 may be in a single device (e.g., the device worn on the individual or watch). The sensing unit 101 may be attached to/comprised in a belt worn on the individual. The sensing unit 101 may be a sensor (e.g., heart activity sensor) which may measure a signal associated with the physiological data, the cardiovascular data or the internal workload from the person's body. The signal may be measured by applying a skin contact from chest, wrist or any other human part. The sensing unit 101 may comprise a second sensor (e.g., motion sensor) which may measure the exercise intensity associated with the external workload. The second sensor may comprise at least one of an accelerometer, a magnetometer and a gyroscope. The sensing unit 101 may further comprise a position sensor (e.g., GPS: Global Positioning System). The sensing unit 101 may comprises at least two sensors described above. The processing unit 102 may be any suitable processing device for executing software instructions, such as a central processing unit (CPU). The processing unit 102 may be a computing unit. The apparatus 100 may comprise at least one device; a first portion of the computing unit may be in one device (e.g., the device worn on the individual or watch), a second portion of the computing unit may be in another device (e.g., mobile device or mobile phone) and a first portion of the computing unit may communicate with a second portion of the computing unit in a wired or wireless way; a first portion of the computing unit and a second portion of the computing unit may be in a single device (e.g., the device worn on the individual or watch). The memory unit 103 may include random access memory (RAM) and read only memory (ROM), but it is not limited to this case. The memory unit 103 may include any suitable non-transitory computer readable medium, such as ROM, CD-ROM, DVD-ROM and so on. Also, the non-transitory computer readable medium is a tangible medium. The non-transitory computer readable medium includes a computer program code which, when executed by the processing unit 102, causes the apparatus 100 to perform desired operations (e.g., operations listed in claims). The display unit 104 may be a display for displaying the degree of response to the physical activity and the optimal suggestion of the physical activity. The displaying mode may be in the form of words, a voice or an image. The sensing unit 101, the processing unit 102, the memory unit 103 and the displaying unit 104 in the apparatus 100 may have any suitable configuration and it doesn't be described in detail therein.

Figure 2:
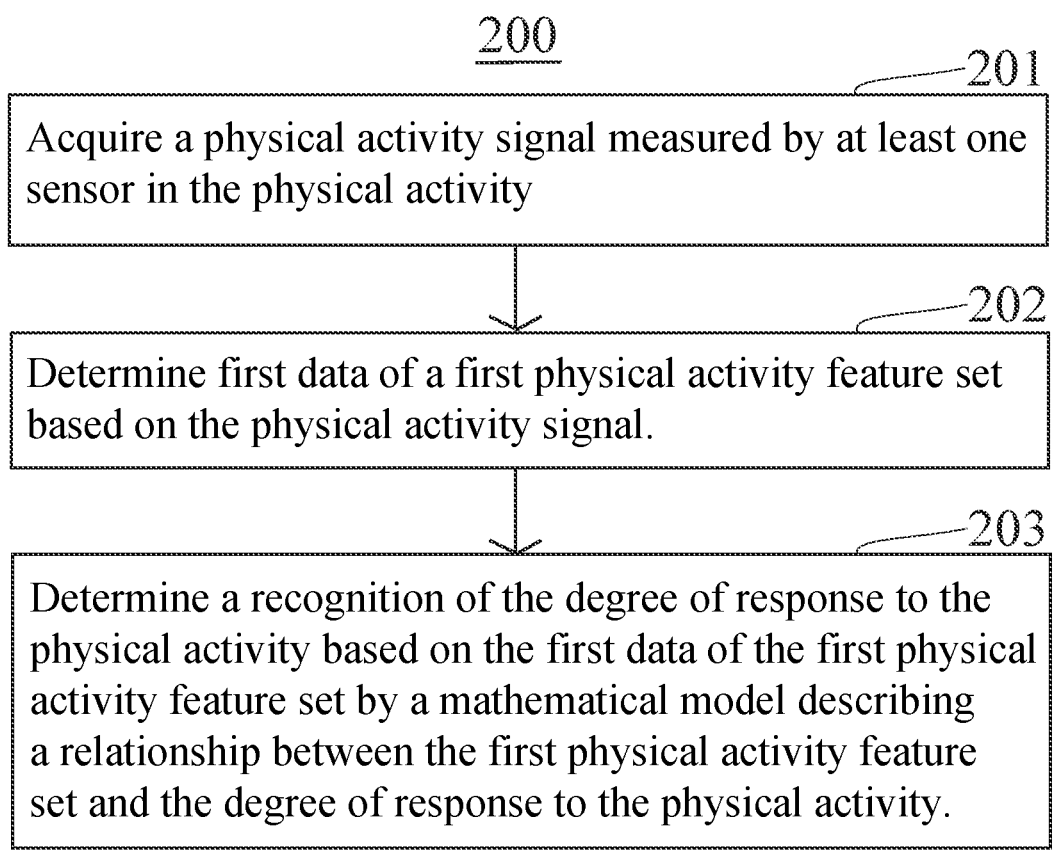
FIG. 2 illustrates a method for determining a degree of response to a physical activity.

FIG. 2 illustrates a method 200 for determining a degree of response to a physical activity. When a person performs a physical activity, the degree of response to the physical activity can be regarded as how much effort made by the person for the physical activity, how the physical activity affects the person or a feedback provided by the person during the physical activity for the stimulus. The method comprises:

Step 201: acquire a physical activity signal measured by at least one sensor in the physical activity;

Step 202: determine first data of a first physical activity feature set based on the physical activity signal; and Step 203: determine a recognition of the degree of response to the physical activity based on the first data of the first physical activity feature set by a mathematical model describing a relationship between the first physical activity feature set and the degree of response to the physical activity.

The most important feature in the present invention is that a portion 312 of a first mechanism 311 of the mathematical model 300 adopts at least one portion 362 of a second mechanism 361 of another (first) neural network model 350 associated with a second physical activity feature set. The first neural network model 350 may describe a relationship between the first physical activity feature set and the second physical activity feature set. The relationship between the mathematical model 300 and another (first) neural network model 350 will be specifically described.

Figure 3A:
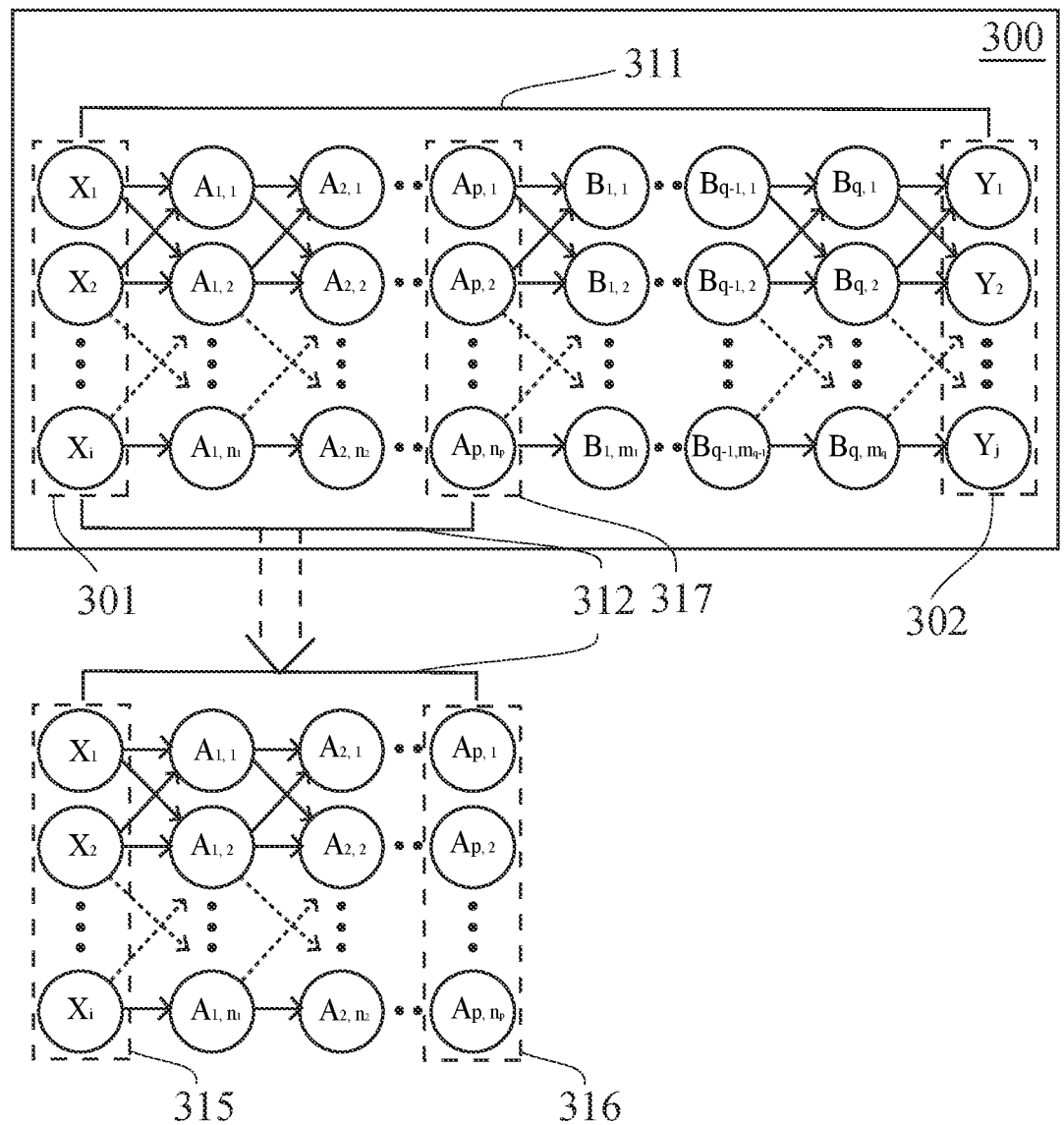
FIG. 3A illustrates a mathematical model in one embodiment of the invention.

FIG. 3A illustrates a mathematical model 300 in one embodiment of the invention. For convenience of description, the mathematical model 300 is represented in the form of the neural network model; however, the present invention is not limited to this case. The mathematical model 300 may comprise a first input layer 301, the first output layer 302 and a plurality of first hidden layers between the first input layer 301 and the first output layer 302. The mathematical model 300 comprises a first mechanism 311 directing the first input layer 301 of the mathematical model 300 to the first output layer 302 of the mathematical model 300. In this case, the first hidden layers comprise the hidden layers I composed of a group of A-symbol-based neurons and the hidden layers II composed of a group of B-symbol-based neurons; the hidden layers I have p layers, the hidden layers II have q layers, and the first hidden layers have p+q layers. The first input layer 301 and the hidden layers I of the mathematical model 300 adopt the second input layer 351 and the hidden layers III of the first neural network model 350 (described hereafter). In each two adjacent layers of the first input layer 301, the first output layer 302 and the first hidden layers, each neuron of the latter layer may be associated with (a combination of) all neurons of the former layer (e.g., a linear combination). Each neuron of the latter layer may be associated with each neuron of the former layer based on a corresponding weight; in other words, each neuron of the former layer is weighted by a corresponding weight, for example, $A_{1,1}=w_1*X_1+w_2*X_2+ \ldots +w_i*X_i$. Besides, the bias and the activation function may be added to determine each neuron.

The first physical activity feature set (e.g., $X_1, X_2, \ldots, X_1$ in FIG. 3A) may be used as the first input layer 301 of the mathematical model 300 and the degree of response to the physical activity (e.g., $Y_1, Y_2, \ldots, Y_j$ in FIG. 3A) may be used as the first output layer 302 of the mathematical model 300.

The first physical activity feature set comprises at least one first feature element. Each (or a portion, or one) of at least one first feature element of the first physical activity feature set may be a heart activity parameter (or a respiratory parameter, e.g., respiration rate). The heart activity parameter may be determined based on a heart activity signal. The heart activity signal may be measured by the heart activity sensor. The heart activity signal may comprise at least one beat and at least one beat interval alternating with the at least one beat; further, the heart activity signal may comprise an interval signal of at least one beat interval, such as RRI (RR interval: beat-to-beat interval extracted from the electrocardiogram (ECG) signal) or PPI (PP interval: beat-to-beat interval extracted from the photoplethysmography (PPG) signal). In other case, the heart activity signal may comprise an EDR (ECG-Derived Respiration) signal or a PDR (PPG-Derived Respiration) signal, a blood pressure signal or a blood oxygen signal. The heart activity parameter may be a heart rate, a pulse rate, RRI, PPI or a parameter determined based on the EDR (ECG-Derived Respiration) signal or the PDR (PPG-Derived Respiration) signal. The heart activity parameter may be a derivative of the previous heart activity parameter or the heart activity parameter may be determined based on another heart activity parameter. For example, the heart rate variability (HRV) information integrates sympathetic and parasympathetic activity of the autonomic nervous system that varies with the degree of response to the physical activity and can be an effective indicator of the degree of response to the physical activity; the heart rate variability (HRV) analysis may be performed to further analyze the beat-to-beat interval to obtain the heart activity parameter, such as a time-domain HRV parameter, a frequency-domain HRV parameter or a non-linear HRV parameter. The time-domain HRV parameter may be determined based on statistics computed over RR interval or PP interval, such as the number of the intervals per epoch, the standard deviation or the mean interval. The time-domain HRV parameter may be a mean of the beat-to-beat interval, a heart rate, a standard deviation of the beat-to-beat interval (e.g., SDNN: Standard Deviation of Normal to Normal) or a root mean square of the adjacent intervals differences (e.g., RMSSD: Root Mean Square of the Successive Differences). The frequency-domain HRV parameter may be determined based on the power spectral analysis of the heart activity. The frequency-domain HRV parameter may be a low frequency range power (LFP), a high frequency range power (HFP) or a ratio (LF/HF) between a high frequency (HF) and a low frequency (LF). The non-linear HRV parameter may be an entropy that measures complexity or regularity of the heart activity.

Each (or a portion, or one) of at least one first feature element of the first physical activity feature set may be a motion parameter. The motion parameter may be determined based on a motion signal. The motion signal may be measured by the motion sensor. The motion signal may be an accelerometer signal, a gyroscope signal, a magnetometer signal, a location signal or a posture signal. The motion parameter may be a speed, an acceleration, an altitude, a location, a power, a force, an energy expenditure rate, a motion intensity, a motion direction, a motion cadence, body movement or a posture change. The motion parameter may be a derivative of the previous motion parameter or the motion parameter may be determined based on another motion parameter. For example, the posture change may be determined based on the location and the body movement.

Each first feature element of a first portion (e.g., $X_1$, $X_2$, ..., $X_a$ in FIG. 3A) of the first physical activity feature set may be a heart activity parameter and each first feature element of a second portion (e.g., $X_{a+1}$, $X_{a+2}$, ..., $X_i$ in FIG. 3A) of the first physical activity feature set may be a motion parameter.

The known correlation (e.g., training set and test set) between the first physical activity feature set and the degree of response to the physical activity may create, generate or define the mathematical model 300. For example, the known correlation (e.g., training set and test set) between the first physical activity feature set and the degree of response to the physical activity may determine a plurality of weights distributed in any two adjacent layers of the first input layer 301, the first output layer 302 and the first hidden layers to create, generate or define the mathematical model 300.

Figure 3B:
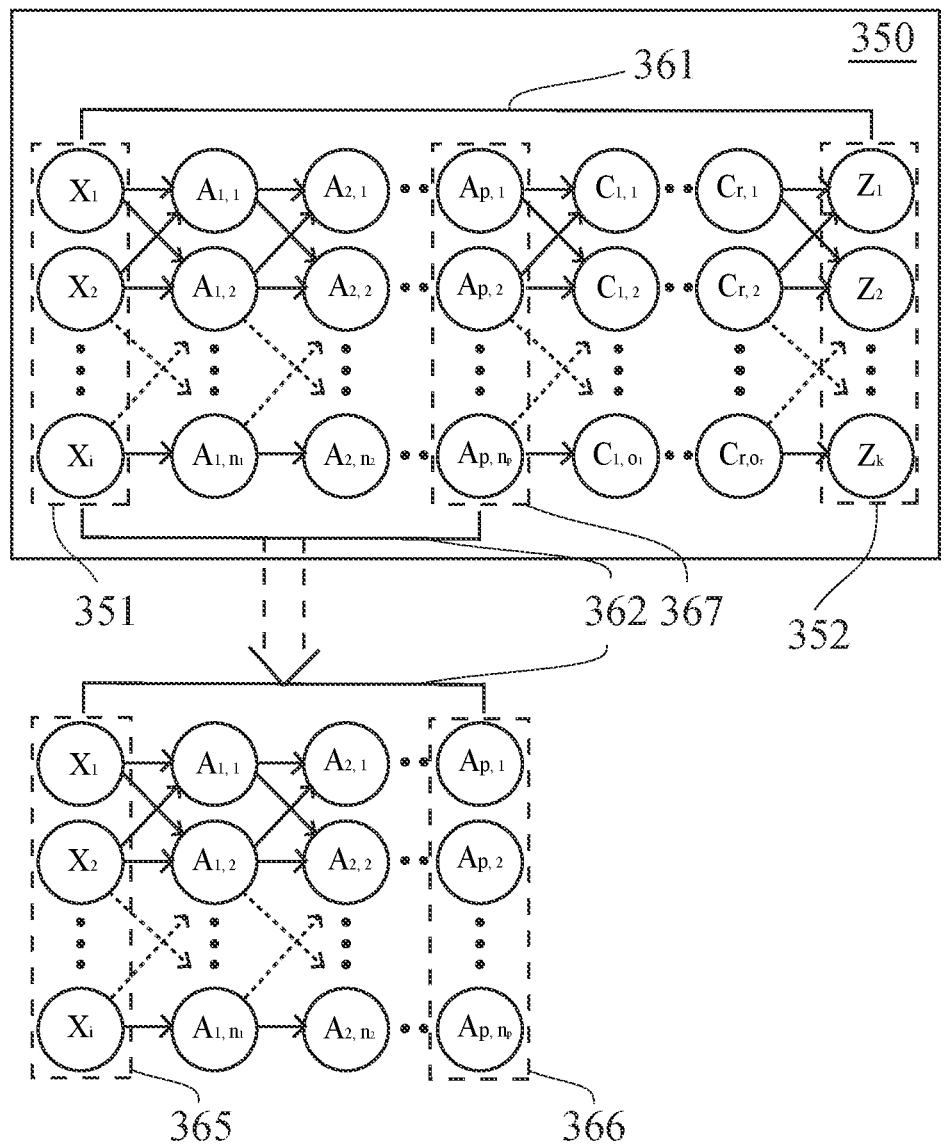
FIG. 3B illustrates a first neural network model corresponding to the mathematical model in FIG. 3A.

FIG. 3B illustrates a first neural network model 350 corresponding to the mathematical model 300 in FIG. 3A. The first neural network model 350 may comprise a second input layer 351, the second output layer 352, and a plurality of second hidden layers between the second input layer 351 and the second output layer 352. The first neural network model 350 comprises a second mechanism 361 directing the second input layer 351 of the first neural network model 350 to the second output layer 352 of the first neural network model 350. In this case, the second hidden layers comprise the hidden layers III composed of a group of A-symbol-based neurons and the hidden layers IV composed of a group of C-symbol-based neurons; the hidden layers III have p layers, the hidden layers IV have r layers, and the second hidden layers have p+r layers. In each two adjacent layers of the second input layer 351, the second output layer 352 and the second hidden layers, each neuron of the latter layer may be associated with (a combination of) all neurons of the former layer (e.g., a linear combination). Each neuron of the latter layer may be associated with each neuron of the former layer based on a corresponding weight; in other words, each neuron of the former layer is weighted by a corresponding weight, for example, $A_{1,1}=w_1*X_1+w_2*X_2+ \ldots +w_i*X_i$. Besides, the bias and the activation function may be added to determine each neuron.

The first physical activity feature set (e.g., $X_1$, $X_2$, ..., $X_i$ in FIG. 3B) may be used as the second input layer 351 of the first neural network model 350 and the second physical activity feature set (e.g., $Z_1$, $Z_2$, ..., $Z_k$ in FIG. 3B) may be used as the second output layer 352 of the first neural network model 350. The first physical activity feature set comprises at least one first feature element and the second physical activity feature set comprises a plurality of second feature elements. The number of at least one first feature element of the first physical activity feature set used as the first input layer 301 of the mathematical model 300 may be the same as the number of at least one first feature element of the first physical activity feature set used as the second input layer 351 of the first neural network model 350. Each of at least one first feature element of the first physical activity feature set used as the first input layer 301 of the mathematical model 300 may be the same as the corresponding first feature element of the first physical activity feature set used as the second input layer 351 of the first neural network model 350. The number of at least one first feature element of the first physical activity feature set may be less than the number of the second feature elements of the second physical activity feature set. The number of the second feature elements of the second physical activity feature set may be more than 5, or 10, or 15, or 20, or 25, or 30, or 35, or 40, or 45, or 50, or 55, or 60, or 65, or 70, or 75, or 80, or 85, or 90, or 95, or 100.

The first physical activity feature set may comprise a plurality of first feature elements; one of the first feature elements is a heart rate. The first physical activity feature set may comprise only one first feature element which is a heart rate because the heart rate is the commonest heart activity parameter easily measured by the heart activity sensor included in the device worn on the individual. The heart rate may be only one heart activity parameter (signal feature) used as the topmost (input) layer of CNN (Convolutional Neural Network) model. Only the data stream of the heart rate may be used as the topmost (input) layer of CNN (Convolutional Neural Network) model.

The first physical activity feature set may have a first feature element not included in the second physical activity feature set. The first physical activity feature set may have a heart rate not included in the second physical activity feature set. Each first feature element of the first physical activity feature set may be not included in the second physical activity feature set. Each second feature element of the second physical activity feature set may be not included in the first physical activity feature set.

The second physical activity feature set comprises at least one second feature element. Each (or a portion, or one) of at least one second feature element of the second physical activity feature set may be a heart activity parameter (or a respiratory parameter, e.g., respiration rate). The heart activity parameter may be determined based on a heart activity signal. The heart activity signal may be measured by the heart activity sensor. The heart activity signal may comprise at least one beat and at least one beat interval alternating with the at least one beat; further, the heart activity signal may comprise an interval signal of at least one beat interval, such as RRI (RR interval: beat-to-beat interval extracted from the electrocardiogram (ECG) signal) or PPI (PP interval: beat-to-beat interval extracted from the photoplethysmography (PPG) signal). In other case, the heart activity signal may comprise an EDR (ECG-Derived Respiration) signal or a PDR (PPG-Derived Respiration) signal, a blood pressure signal or a blood oxygen signal. The heart activity parameter may be a heart rate, a pulse rate, RRI, PPI or a parameter determined based on the EDR (ECG-Derived Respiration) signal or the PDR (PPG-Derived Respiration) signal. The heart activity parameter may be a derivative of the previous heart activity parameter or the heart activity parameter may be determined based on another heart activity parameter. For example, the heart rate variability (HRV) information integrates sympathetic and parasympathetic activity of the autonomic nervous system that varies with the degree of response to the physical activity and can be an effective indicator of the degree of response to the physical activity; the heart rate variability (HRV) analysis may be performed to further analyze the beat-to-beat interval to obtain the heart activity parameter, such as a time-domain HRV parameter, a frequency-domain HRV parameter or a non-linear HRV parameter. The time-domain HRV parameter may be determined based on statistics computed over RR interval or PP interval, such as the number of the intervals per epoch, the standard deviation or the mean interval. The time-domain HRV parameter may be a mean of the beat-to-beat interval, a heart rate, a standard deviation of the beat-to-beat interval (e.g., SDNN: Standard Deviation of Normal to Normal) or a root mean square of the adjacent intervals differences (e.g., RMSSD: Root Mean Square of the Successive Differences). The frequency-domain HRV parameter may be determined based on the power spectral analysis of the heart activity. The frequency-domain HRV parameter may be a low frequency range power (LFP), a high frequency range power (HFP) or a ratio (LF/HF) between a high frequency (HF) and a low frequency (LF). The non-linear HRV parameter may be an entropy that measures complexity or regularity of the heart activity.

Each (or a portion, or one) of at least one second feature element of the second physical activity feature set may be a motion parameter. The motion parameter may be determined based on a motion signal. The motion signal may be measured by the motion sensor. The motion signal may be an accelerometer signal, a gyroscope signal, a magnetometer signal, a location signal or a posture signal. The motion parameter may be a speed, an acceleration, an altitude, a location, a power, a force, an energy expenditure rate, a motion intensity, a motion direction, a motion cadence, body movement or a posture change. The motion parameter may be a derivative of the previous motion parameter or the motion parameter may be determined based on another motion parameter. For example, the posture change may be determined based on the location and the body movement.

Each second feature element of a first portion (e.g., $Z_1$, $Z_2$, ..., $Z_b$ in FIG. 3B) of the second physical activity feature set may be a heart activity parameter and each second feature element of a second portion (e.g., $Z_{b+1}$, $Z_{b+2}$, ..., $Z_k$ in FIG. 3B) of the second physical activity feature set may a be motion parameter.

In a first embodiment of a combination of the first physical activity feature set and the second physical activity feature set, each of at least one first feature element of the first physical activity feature set may be a heart activity parameter and each of at least one second feature element of the second physical activity feature set may be also a heart activity parameter. Each first feature element of the first physical activity feature set may be a heart activity parameter and each second feature element of the second physical activity feature set may be also a heart activity parameter. The heart activity parameter may be determined based on the heart activity signal. The heart activity signal may be measured the heart activity sensor. The heart activity parameter is determined based on at least one beat and at least one beat interval alternating with the at least one beat of the heart activity signal. The heart activity parameter is determined based on an interval signal of at least one beat interval of the heart activity signal (e.g., RRI (RR interval) or PPI (PP interval)).

In a second embodiment of a combination of the first physical activity feature set and the second physical activity feature set, each of at least first feature element of the first physical activity feature set may be a motion parameter and each of at least one second feature element of the second physical activity feature set may be also a motion parameter. Each first feature element of the first physical activity feature set may be a motion parameter and each second feature element of the second physical activity feature set may be also a motion parameter. The motion parameter is determined based on the motion signal. The motion signal is measured by the motion sensor.

In a third embodiment of a combination of the first physical activity feature set and the second physical activity feature set, each of at least one first feature element of the first physical activity feature set may be a heart activity parameter and each of at least one second feature element of the second physical activity feature set may be a motion parameter. Each first feature element of the first physical activity feature set may be a heart activity parameter and each second feature element of the second physical activity feature set may be a motion parameter. The heart activity parameter is determined based on at least one beat and at least one beat interval alternating with the at least one beat of the heart activity signal. The heart activity parameter is determined based on an interval signal of at least one beat interval of the heart activity signal (e.g., RRI (RR interval) or PPI (PP interval). The motion parameter is determined based on the motion signal. The motion signal is measured by the motion sensor.

In a fourth embodiment of a combination of the first physical activity feature set and the second physical activity feature set, each of at least one of first feature element of the first physical activity feature set may be a motion parameter and each of at least one second feature element of the second physical activity feature set may be a heart activity parameter. Each first feature element of the first physical activity feature set may be a motion parameter and each second feature element of the second physical activity feature set may be a heart activity parameter. The heart activity parameter is determined based on at least one beat and at least one beat interval alternating with the at least one beat of the heart activity signal. The heart activity parameter is determined based on an interval signal of at least one beat interval of the heart activity signal (e.g., RRI (RR interval) or PPI (PP interval). The motion parameter is determined based on the motion signal. The motion signal is measured by the motion sensor.

The known correlation (e.g., training set and test set) between the first physical activity feature set and the second physical activity feature set may create, generate or define the first neural network model 350. For example, the known correlation (e.g., training set and test set) between the first physical activity feature set and the second physical activity feature set may determine a plurality of weights distributed in any two adjacent layers of the second input layer 351, the second output layer 352 and the second hidden layers to create, generate or define the first neural network model 350.

A first portion 312 of the first mechanism 311 of the mathematical model 300 directs the first topmost layer 315 of the first portion 312 of the first mechanism 311 to the first bottommost layer 316 of the first portion 312 of the first mechanism 311. The first bottommost layer 316 of the first mechanism 311 of the mathematical model 300 is not used as the first output layer 302 of the mathematical model 300. At least one second portion 362 of the second mechanism 361 of the first neural network model 350 directs the second topmost layer 365 of at least one second portion 362 of the second mechanism 361 to the second bottommost layer 366 of at least one second portion 362 of the second mechanism 361. The first portion 312 of the first mechanism 311 of the mathematical model 300 adopts the at least one second portion 362 of the second mechanism 361 of the first neural network model 350 with the first topmost layer 315 being the second topmost layer 365 and the first bottommost layer 316 being the second bottommost layer 366. In one embodiment, the layer number of the mathematical model 300 is more than the layer number of the first neural network model 350 if the first portion 312 of the first mechanism 311 of the mathematical model 300 adopts the overall the second mechanism 361 of the first neural network model 350.

The first neural network model 350 may be a DNN (Deep Neural Network) model, a CNN (Convolutional Neural Network) model, a RNN (Recurrent Neural Network) model or a combination thereof. The mathematical model 300 may be a neural network model, such as DNN model, CNN model, RNN model or a combination thereof. The mathematical model 300 may be a complete neural network model. The mathematical model 300 may be a combination of mathematical sub-models and one of the mathematical sub-models is a neural network model or associated with a neural network model, such as DNN model, CNN model or RNN model. For example, the first portion 312 of the first mechanism 311 of the mathematical model 300 adopts at least one second portion 362 of the second mechanism 361 of the first neural network model 350 such that the mathematical sub-model used in the first portion 312 of the first mechanism 311 of the mathematical model 300 is a neural network model and the remaining portion of the first mechanism 311 of the mathematical model 300 may include decision tree (including gradient boosting and random forest), support vector machine, linear regression, logistic regression or neural network.

Specifically speaking, the first topmost layer 315 of the first portion 312 of the first mechanism 311 of the mathematical model 300 is used as the first input layer 301 of the mathematical model 300 and the first bottommost layer 316 of the first portion 312 of the first mechanism 311 of the mathematical model 300 is used as the medium layer 317 of the mathematical model 300 between the first input layer 301 and the first output layer 302 (see FIG. 3A); the second topmost layer 365 of the at least one second portion 362 of the second mechanism 361 of the first neural network model 350 is used as the second input layer 351 of the first neural network model 350 and the second bottommost layer 366 of the at least one second portion 362 of the second mechanism 361 of the first neural network model 350 is used as the medium layer 367 of the first neural network model 350 between the second input layer 351 and the second output layer 352 (see FIG. 3B).

In another embodiment, the second topmost layer 365 of the at least one second portion 362 of the second mechanism 361 of the first neural network model 350 is used as the second input layer 351 of the first neural network model 350 and the second bottommost layer 366 of the at least one second portion 362 of the second mechanism 361 of the first neural network model 350 is used as a second output layer 352 of the first neural network model 350; the first topmost layer 315 of the first portion 312 of the first mechanism 311 of the mathematical model 300 is used as the first input layer 301 of the mathematical model 300 and the first bottommost layer 316 of the first portion 312 of the first mechanism 311 of the mathematical model 300 is used as a medium layer of the mathematical model 300 corresponding to the second output layer 352 of the first neural network model 350.

Figure 4A:
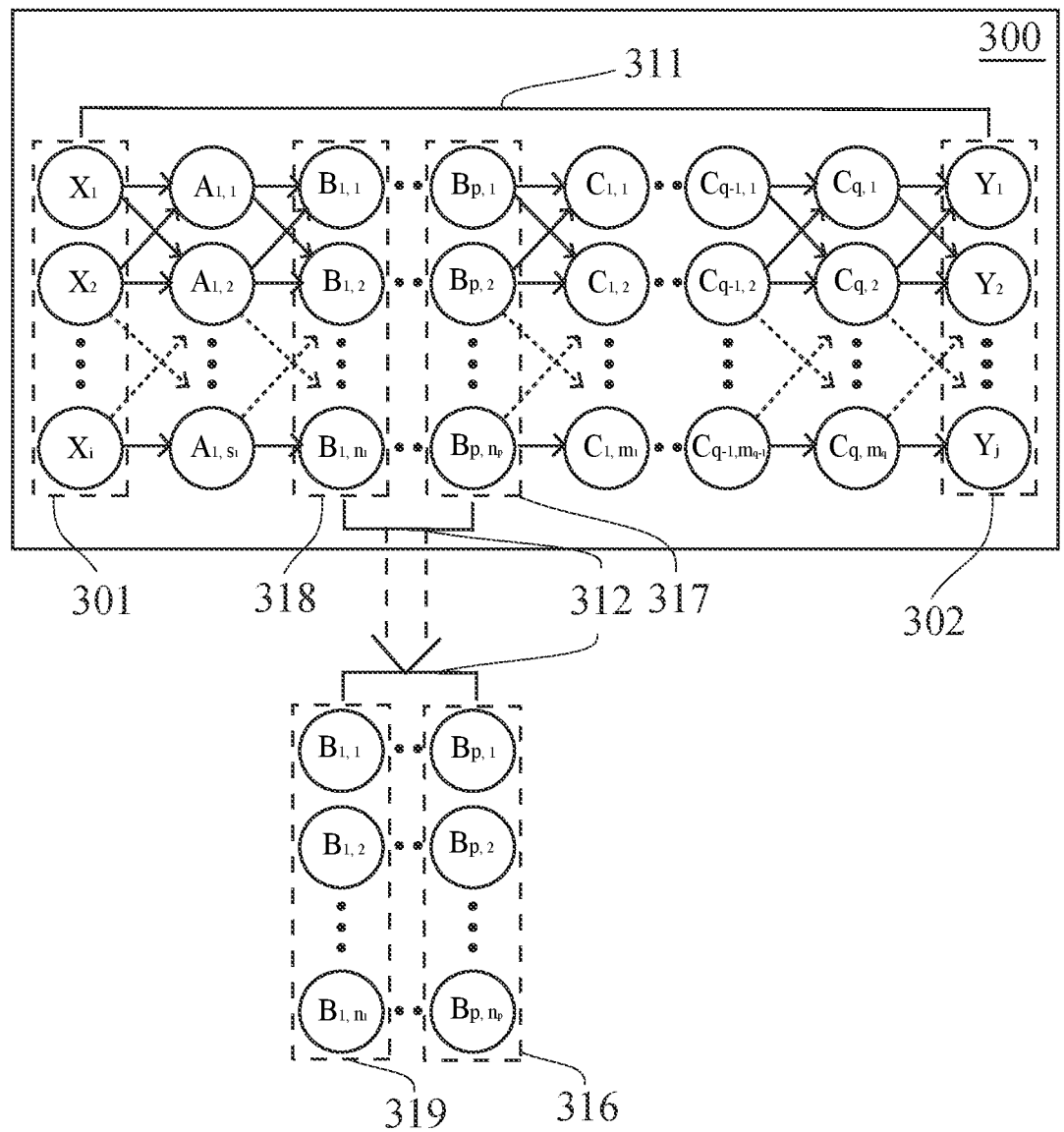
FIG. 4A illustrates a mathematical model in another embodiment of the invention.
Figure 4B:
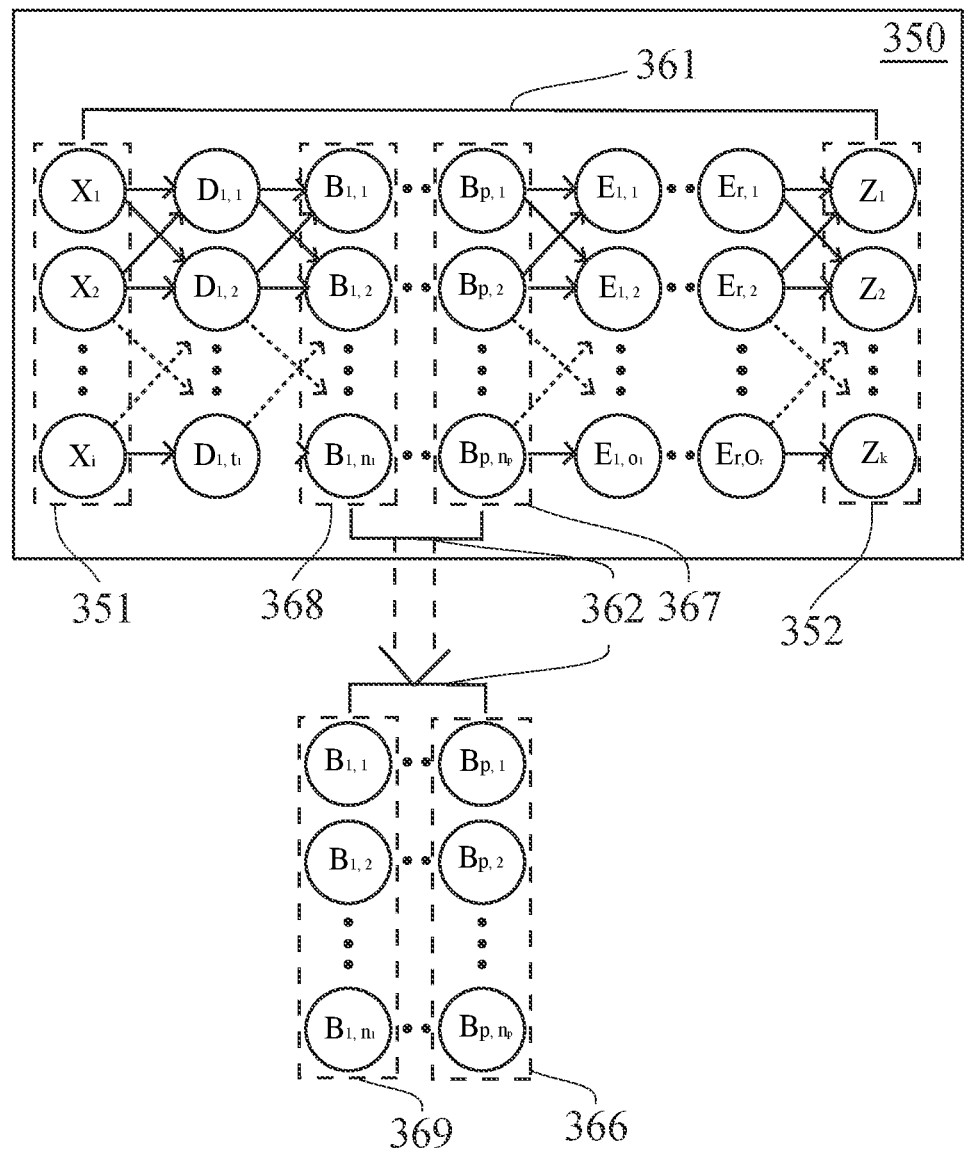
FIG. 4B illustrates the first neural network model corresponding to the mathematical model in FIG. 4A.

FIG. 4A illustrates a mathematical model 300 in another embodiment of the invention. FIG. 4B illustrates the first neural network model 350 corresponding to the mathematical model 300 in FIG. 4A. For convenience of description, the mathematical model 300 is represented in the form of the neural network model; however, the present invention is not limited to this case.

Compared to the mathematical model 300 in FIG. 3A, the first topmost layer 319 of the first portion 312 of the first mechanism 311 of the mathematical model 300 is used as the medium layer 318 of the mathematical model 300 and the first bottommost layer 316 of the first portion 312 of the first mechanism 311 of the mathematical model 300 is used as the medium layer 317 of the mathematical model 300 in FIG. 4A. The first input layer 301, the medium layer 318, the medium layer 317 and the first output layer 302 of the mathematical model 300 are arranged in an order. In this case, the first hidden layers comprise the hidden layer I composed of a group of A-symbol-based neurons, the hidden layers II composed of a group of B-symbol-based neurons and the hidden layers III composed of a group of C-symbol-based neurons; the hidden layer I has 1 layer, the hidden layers II have p layers, the hidden layers III have q layers, and the first hidden layers have 1+p+q layers. The hidden layers II of the mathematical model 300 adopt the hidden layers V of the first neural network model 350. In each two adjacent layers of the first input layer 301, the first output layer 302 and the first hidden layers, each neuron of the latter layer may be associated with (a combination of) all neurons of the former layer (e.g., a linear combination). Each neuron of the latter layer may be associated with each neuron of the former layer based on a corresponding weight; in other words, each neuron of the former layer is weighted by a corresponding weight, for example, $A_{1,1}=w_1*X_1+w_2*X_2+ \ldots +w_i*X_i$. Besides, an activation function may be added to determine each neuron.

Compared to the first neural network model 350 in FIG. 3B, the second topmost layer 369 of the at least one second portion 362 of the second mechanism 361 of the first neural network model 350 is used as the medium layer 368 of the first neural network model 350 and the second bottommost layer 366 of the at least one second portion 362 of the second mechanism 361 of the first neural network model 350 is used as the medium layer 367 of the first neural network model 350 in FIG. 4B. The second input layer 351, the medium layer 368, the medium layer 367 and the second output layer 352 are arranged in an order. In this case, the second hidden layers comprise the hidden layer IV composed of a group of D-symbol-based neurons, the hidden layers V composed of a group of B-symbol-based neurons and the hidden layers VI composed of a group of E-symbol-based neurons; the hidden layer IV has 1 layer, the hidden layers V have p layers, the hidden layers VI have r layers, and the second hidden layers have 1+p+r layers. In each two adjacent layers of the second input layer 351, the second output layer 352 and the second hidden layers, each neuron of the latter layer may be associated with (a combination of) all neurons of the former layer (e.g., a linear combination). Each neuron of the latter layer may be associated with each neuron of the former layer based on a corresponding weight; in other words, each neuron of the former layer is weighted by a corresponding weight, for example, $D_{1,1}=w_1*X_1+w_2*X_2+ \ldots +w_i*X_i$. Besides, an activation function may be added to determine each neuron.

If one first feature element of the first physical activity feature set is a heart activity parameter in the above description, the heart activity parameter may be a heart rate. The first physical activity feature set may comprise only one first feature element which is a heart rate because the heart rate is the commonest heart activity parameter easily measured by the heart activity sensor included in the device worn on the individual. The heart rate may be only one heart activity parameter (signal feature) used as the topmost (input) layer of CNN (Convolutional Neural Network) model. Only the data stream of the heart rate may be used as the topmost (input) layer of CNN (Convolutional Neural Network) model.

The present invention builds up a mathematical model 300 for determining a recognition of the degree of response to the physical activity performed by the person based on the measured data of the first physical activity feature set (i.e., the first input layer 301) by the mathematical model 300 describing a relationship between the first physical activity feature set and the degree of response to the physical activity. A portion 312 of the first mechanism 311 of the mathematical model 300 adopts at least one portion 362 of the second mechanism 361 of the first neural network model 350 associated with the second physical activity feature set (i.e., the second output layer 352). Specifically, besides the first physical activity feature set generally used as the input layer 301 of the mathematical model 300 for determining the degree of response to the physical activity performed by the person, at least one portion 362 of the second mechanism 361 of another neural network model 350 also becomes a portion of the first mechanism 311 of the mathematical model 300. Because the first mechanism 311 of the mathematical model 300 further takes into account the neural network feature derived from the second physical activity feature set highly correlated with the degree of response to the physical activity performed by the person, at least one portion 362 of the second mechanism 361 of another neural network model 350 becoming a portion of the first mechanism 311 of the mathematical model 300 can increase a precision of determining the degree of response to the physical activity performed by the person.

The first physical activity feature set and the second physical activity feature set are both correlated with the degree of response to the physical activity performed by the person. The first physical activity feature set is correlated with the second physical activity feature set. Each of the first physical activity feature set and the second physical activity feature set may have the derivative information having a portion of information useful for determining the degree of response to the physical activity performed by the person and a remaining portion of information not useful for determining the degree of response to the physical activity performed by the person. The derivative information of the first physical activity feature set may be different from the derivative information of the second physical activity feature set. Besides, the useful rate of the derivative information of the first physical activity feature set may be different from the useful rate of the derivative information of the second physical activity feature set (the useful rate of the derivative information is the ratio of a portion of the derivative information useful for determining the degree of response to the physical activity performed by the person to the derivative information). By the first neural network model 350 associating the first physical activity feature set with the second physical activity feature set and a portion 312 of the first mechanism 311 of the mathematical model 300 adopting at least one portion 362 of the second mechanism 361 of the first neural network model 350, the features used as the bottommost layer 317 of a portion 312 of the first mechanism 311 of the mathematical model 300 may have the optimal derivative information and the optimal useful rate of the derivative information such that a portion 312 of the first mechanism 311 of the mathematical model 300 adopting at least one portion 362 of the second mechanism 361 of the first neural network model 350 can increase a precision of determining the degree of response to the physical activity performed by the person after the mathematical model 300 is trained.

There is another technical advantage in the present invention. The mathematical model 300 can only rely on a first sensing hardware unit measuring the physical activity signal used for determining the first data of the first physical activity feature set after the mathematical model 300 is trained, without another sensing hardware unit measuring the physical activity signal used for determining the second data of the second physical activity feature set. As described above, the second physical activity feature set can be a hidden input layer of the mathematical model 300 and thus another sensing hardware unit may be not needed. Therefore, the cost and the related measurement equipment of another sensing hardware can be saved.

In some case, the physical activity signal used for determining the second data of the second physical activity feature set is unable to be measured by the first sensing unit and can be measured by another sensing unit different from the first sensing unit (the second data of the second physical activity feature set may be used for training the first neural network model 350). Take the physical activity being sleep and the degree of response to the physical activity being the sleep stage (or any other response to sleep, e.g., sleep quality) for example. The first physical activity feature set comprises a heart rate determined based on the heart activity signal measured by the heart rate sensor or a heart activity parameter determined based on at least one beat and at least one beat interval alternating with the at least one beat of the heart activity signal (measured by the heart activity sensor). The second physical activity feature set comprises at least one (or all) of the second feature element(s) determined based on at least one (or all) of the electroencephalography (EEG) signal, the electrooculography (EOG) signal and the electromyography (EMG) signal measured the corresponding sensors associated with polysomnography (PSG) but not based on the heart activity signal measured by the heart rate sensor or the heart activity sensor. In this example, the measurement equipment associated with polysomnography (PSG) is much more expensive than the heart rate measurement equipment (e.g., heart rate sensor); once the first neural network model 350 is trained and a portion 312 of the first mechanism 311 of the mathematical model 300 adopts at least one portion 362 of the second mechanism 361 of the first neural network model 350 associated with the second physical activity feature set, the second physical activity feature set determined based on the electroencephalography (EEG) signal, the electrooculography (EOG) signal or the electromyography (EMG) signal can be a hidden input mode of the mathematical model 300 and thus the measurement equipment associated with polysomnography (PSG) is not needed. Therefore, the cost of the measurement equipment associated with polysomnography (PSG) can be saved. Moreover, the electroencephalography (EEG) signal, the electrooculography (EOG) signal or the electromyography (EMG) signal are highly correlated with the sleep stage (or any other response to sleep, e.g., sleep quality), the mathematical model 300 having a hidden input mode associated with the electroencephalography (EEG) signal, the electrooculography (EOG) signal or the electromyography (EMG) signal can increase a precision of determining the sleep stage (or any other response to sleep, e.g., sleep quality).

After the first neural network model 350 is built up, a portion 312 of the first mechanism 311 of the mathematical model 300 adopts at least one portion 362 of the second mechanism 361 of the first neural network model 350 associated with the second physical activity feature set (i.e., the second output layer 352) with the determined values of the weights in at least one portion 362 of the second mechanism 361 of the first neural network model 350 being used as the initial values of the weights in a portion 312 of the first mechanism 311 of the mathematical model 300 before the mathematical model 300 is building up for determining the recognition of the degree of response to the physical activity performed by the person.

In one embodiment, the final values of the weights in a portion 312 of the first mechanism 311 of the mathematical model 300 are the same as the determined values of the weights of at least one portion 362 of the second mechanism 361 of the first neural network model 350 after the mathematical model 300 is built up for determining the recognition of the degree of response to the physical activity performed by the person. In other words, only the remaining portion of the first mechanism 311 (a combination of a portion 312 and the remaining portion of the first mechanism 311) of the mathematical model 300 configured to match a portion 312 of the first mechanism 311 of the mathematical model 300 is trained to build up the mathematical model 300; the final values of the weights in a portion 312 of the first mechanism 311 of the mathematical model 300 after the mathematical model 300 is building up are the same as the initial values of the weights in a portion 312 of the first mechanism 311 of the mathematical model 300 before the mathematical model 300 is building up.

In another embodiment, the final values of the weights in a portion 312 of the first mechanism 311 of the mathematical model 300 are trained to be different the determined values of the weights of at least one portion 362 of the second mechanism 361 of the first neural network model 350 after the mathematical model 300 is built up for determining the recognition of the degree of response to the physical activity performed by the person. In other words, the remaining portion (a combination of a portion 312 and the remaining portion of the first mechanism 311) of the first mechanism 311 of the mathematical model 300 configured to match a portion 312 of the first mechanism 311 of the mathematical model 300 and a portion 312 of the first mechanism 311 of the mathematical model 300 are both trained to build up the mathematical model 300; the final values of the weights in a portion 312 of the first mechanism 311 of the mathematical model 300 after the mathematical model 300 is building up are is different from the initial values of the weights in a portion 312 of the first mechanism 311 of the mathematical model 300 before the mathematical model 300 is building up.

The mathematical model 300 used for determining a degree of response to the physical activity performed by the person may be applied in all kinds of applications. For example, the physical activity may be sleep and the degree of response to the physical activity may be the sleep stage or any other response to sleep (e.g., sleep quality). For example, the physical activity may be any activity and the degree of response to the physical activity may be represented in the form of the stress. For example, the physical activity may be an exercise and the degree of response to the physical activity may be fatigue or tiredness; however, the present invention is not limited to these cases.

The degree of response to the physical activity may be represented in the form of the index or the level. The degree of response to the physical activity may be classified into a plurality of phases or states. Choose one of phases or states as the degree of response to the physical activity may be based on the probability of each phase or state.

Take the physical activity being sleep and the degree of response to the physical activity being the sleep stage (or any other response to sleep, e.g., sleep quality) for example.

The sleep stage may refer to one or more phases or states of sleep and each recognized phase or state has a particular physiological feature. These phases and states may be known in the art. For example, the sleep stages include an awake stage, a REM (rapid eye movement) stage or a NREM (non-rapid eye movement) stage; the NREM stage includes a stage N1, a stage N2, a stage N3 or a stage N4. The sleep stage may correspond to a single recognized phase or state. The sleep stage may correspond to multiple recognized phases or states of sleep. For example, the stages N1-N4 may be collectively a NREM stage. In another example, stages N3 and N4 may constitute a single stage. Certain stages may be labeled, such as "deep sleep," "light sleep" or any other descriptive phrase. After the definition of each sleep stage and the number of the overall sleep stages is identified, the overall sleep stages may be used as first output layer 302 of the mathematical model 300.

Conventionally, recognizing the sleep stage (or any other response to sleep, e.g., sleep quality) requires the specialized data processing devices which are costly or cumbersome; for example, the specialized data processing devices used in polysomnography (PSG) may include the hardware equipment associated with electroencephalography (EEG), electrooculography (EOG) or electromyography (EMG). Take using the present invention to recognize the sleep stage (or any other response to sleep, e.g., sleep quality) for example. The data (e.g., the first data of the first physical activity feature set) is measured by at least one sensor included in the device worn on the individual or the portable device (e.g., mobile device, mobile phone). The data may come from the electrocardiogram (ECG) signal, the photoplethysmography (PPG) signal or the motion signal. The data measured by at least one sensor is used as the first input layer 301 of the mathematical model 300 to determine the sleep stage. In one embodiment, the sleep stage at the current time may be determined further based on the sleep stage at the previous time. Using the mathematical model 300 may provide more accurate measurements of an individual's sleep stage (or any other response to sleep, e.g., sleep quality) without needing additional costly or cumbersome equipment (e.g., the hardware equipment associated with electroencephalography (EEG), electrooculography (EOG) or electromyography (EMG).

The above disclosure is related to the detailed technical contents and inventive features thereof. People skilled in the art may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A method for determining a degree of response to a physical activity, the method comprising:
   acquiring a physical activity signal measured by at least one sensor in the physical activity;
   determining, by a processing unit, first data of a first physical activity feature set based on the physical activity signal; and
   determining, by the processing unit, a recognition of the degree of response to the physical activity based on the first data of the first physical activity feature set by a mathematical model describing a relationship between the first physical activity feature set and the degree of response to the physical activity;

wherein the mathematical model comprises a first mechanism directing a first input layer of the mathematical model to a first output layer of the mathematical model, wherein the first physical activity feature set is used as the first input layer of the mathematical model and the degree of response to the physical activity is used as the first output layer of the mathematical model;

wherein a first neural network model comprises a second mechanism directing a second input layer of the first neural network model to a second output layer of the first neural network model, wherein the first physical activity feature set is used as the second input layer of the first neural network model and a second physical activity feature set is used as the second output layer of the first neural network model;

wherein a first portion of the first mechanism directs a first topmost layer of the first portion of the first mechanism to a first bottommost layer of the first portion of the first mechanism, and at least one second portion of the second mechanism directs a second topmost layer of the at least one second portion of the second mechanism to a second bottommost layer of the at least one second portion of the second mechanism, wherein the first bottommost layer of the first portion of the first mechanism is not used as the first output layer of the mathematical model;

wherein the first portion of the first mechanism of the mathematical model adopts the at least one second portion of the second mechanism of the first neural network model with the first topmost layer being the second topmost layer and the first bottommost layer being the second bottommost layer.

2. The method according to claim 1, wherein the first portion of the first mechanism has a plurality of first weights assisting in directing the first topmost layer of the first portion of the first mechanism to the first bottommost layer of the first portion of the first mechanism and the at least one second portion of the second mechanism has a plurality of second weights assisting in directing the second topmost layer of the at least one second portion of the second mechanism to the second bottommost layer of the at least one second portion of the second mechanism, wherein the determined values of the plurality of second weights are used as the initial values of the plurality of first weights before the mathematical model is building up for determining the recognition of the degree of response to the physical activity.

3. The method according to claim 2, wherein the final values of the plurality of first weights are the same as the determined values of the plurality of second weights after mathematical model is built up for determining the recognition of the degree of response to the physical activity.

4. The method according to claim 2, wherein the final values of the plurality of first weights are trained to be different from the determined values of the plurality of second weights after the mathematical model is built up for determining the recognition of the degree of response to the physical activity.

5. The method according to claim 1, wherein the first topmost layer of the first portion of the first mechanism is used as the first input layer of the mathematical model and the first bottommost layer of the first portion of the first mechanism is used as a first medium layer of the mathematical model between the first input layer and the first output layer, wherein the second topmost layer of the at least one second portion of the second mechanism is used as the second input layer of the first neural network model and the second bottommost layer of the at least one second portion of the second mechanism is used as a second medium layer of the first neural network model between the second input layer and the second output layer.

6. The method according to claim 1, wherein the first topmost layer of the first portion of the first mechanism is used as a first medium layer of the mathematical model and the first bottommost layer of the first portion of the first mechanism is used as a second medium layer of the mathematical model, wherein the first input layer, the first medium layer, the second medium layer and the first output layer of the mathematical model are arranged in a first order.

7. The method according to claim 1, wherein the first physical activity feature set comprises at least one first feature element, wherein one of the at least one first feature element is a heart rate.

8. The method according to claim 1, wherein the first physical activity feature set has a first feature element not included in the second physical activity feature set.

9. The method according to claim 8, wherein the first feature element is a heart rate.

10. The method according to claim 1, wherein the first physical activity feature set comprises at least one first feature element and the second physical activity feature set comprises at least one second feature element, wherein each of the at least one first feature element of the first physical activity feature set is a first heart activity parameter and each of the at least one second feature element of the second physical activity feature set is a second heart activity parameter.

11. The method according to claim 10, wherein the first heart activity parameter and the second heart activity parameter are determined based on at least one beat and at least one beat interval alternating with the at least one beat of a heart activity signal.

12. The method according to claim 10, wherein the first heart activity parameter and the second heart activity parameter are determined based on an interval signal of at least one beat interval of a heart activity signal.

13. The method according to claim 1, wherein the first physical activity feature set comprises at least one first feature element and the second physical activity feature set comprises at least one second feature element, wherein each of the at least one first feature element of the first physical activity feature set is a first motion parameter and each of the at least one second feature element of the second physical activity feature set is a second motion parameter.

14. The method according to claim 1, wherein the first physical activity feature set comprises at least one first feature element and the second physical activity feature set comprises at least one second feature element, wherein each of the at least one first feature element of the first physical activity feature set is a heart activity parameter and each of the at least one second feature element of the second physical activity feature set is a motion parameter.

15. The method according to claim 1, wherein the first physical activity feature set comprises at least one first feature element and the second physical activity feature set comprises at least one second feature element, wherein each of the at least one first feature element of the first physical activity feature set is a motion parameter and each of the at least one second feature element of the second physical activity feature set is a heart activity parameter.

16. The method according to claim 1, wherein the first physical activity feature set comprises a plurality of feature elements, wherein each feature element of a first portion of the first physical activity feature set is a heart activity parameter and each feature element of a second portion of the first physical activity feature set is a motion parameter.

17. The method according to claim 1, wherein the second physical activity feature set comprises a plurality of feature elements, wherein each feature element of a first portion of the second physical activity feature set is a heart activity parameter and each feature element of a second portion of the second physical activity feature set is a motion parameter.

18. The method according to claim 1, wherein the mathematical model is a second neural network model.

19. The method according to claim 1, wherein the first neural network model is a CNN (Convolutional Neural Network) model.

20. The method according to claim 1, wherein the physical activity is sleep and the degree of response to the physical activity is a sleep stage.

21. The method according to claim 20, wherein the first physical activity feature set comprises at least one first feature element, wherein one of the at least one first feature element is a heart rate, wherein the second physical activity feature set comprises at least one second feature element, wherein the at least one second feature element is determined based on at least one of an electroencephalography (EEG) signal, an electrooculography (EOG) signal and an electromyography (EMG) signal.

22. The method according to claim 20, wherein the first physical activity feature set comprises at least one first feature element, wherein one of the at least one first feature element is a heart activity parameter determined based on at least one beat and at least one beat interval alternating with the at least one beat of a heart activity signal, wherein the second physical activity feature set comprises at least one second feature element, wherein the at least one second feature element is determined based on at least one of an electroencephalography (EEG) signal, an electrooculography (EOG) signal and an electromyography (EMG) signal.

23. A method for determining a degree of response to a physical activity, the method comprising:
acquiring a first physical activity signal measured by a first sensing unit in the physical activity;
determining, by a processing unit, first data of a first physical activity feature set based on the first physical activity signal; and
determining, by the processing unit, a recognition of the degree of response to the physical activity based on the first data of the first physical activity feature set by a mathematical model describing a first relationship between the first physical activity feature set and the degree of response to the physical activity;
wherein a portion of a first mechanism of the mathematical model adopts at least one portion of a second mechanism of a first neural network model associated with a second physical activity feature set, the first physical activity feature set has at least one first feature element and the second physical activity feature set has a plurality of second feature elements, and a first number of the at least one first feature element is less than a second number of the plurality of second feature elements.

24. A method for determining a degree of response to a physical activity, the method comprising:
acquiring a physical activity signal measured by at least one sensor in the physical activity;
determining, by a processing unit, first data of a first physical activity feature set based on the physical activity signal; and
determining, by the processing unit, a recognition of the degree of response to the physical activity based on the first data of the first physical activity feature set by a mathematical model describing a relationship between the first physical activity feature set and the degree of response to the physical activity;
wherein the mathematical model comprises a first mechanism directing a first input layer of the mathematical model to a first output layer of the mathematical model, wherein the first physical activity feature set is used as the first input layer of the mathematical model and the degree of response to the physical activity is used as the first output layer of the mathematical model, wherein the first physical activity feature set comprises at least one first feature element, wherein one of the at least one first feature element of the first physical activity feature set is a heart rate;
wherein a first neural network model comprises a second mechanism directing a second input layer of the first neural network model to a second output layer of the first neural network model, wherein the first physical activity feature set is used as the second input layer of the first neural network model and a second physical activity feature set is used as the second output layer of the first neural network model, wherein the second physical activity feature set comprises at least one second feature element, wherein one of the at least one second feature element of the second physical activity feature set is a heart activity parameter determined based on at least one beat and at least one beat interval alternating with the at least one beat of a heart activity signal;
wherein a first portion of the first mechanism directs a first topmost layer of the first portion of the first mechanism to a first bottommost layer of the first portion of the first mechanism, and at least one second portion of the second mechanism directs a second topmost layer of the at least one second portion of the second mechanism to a second bottommost layer of the at least one second portion of the second mechanism, wherein the first bottommost layer of the first portion of the first mechanism is not used as the first output layer of the mathematical model;
wherein the first portion of the first mechanism of the mathematical model adopts the at least one second portion of the second mechanism of the first neural network model with the first topmost layer being the second topmost layer and the first bottommost layer being the second bottommost layer.

25. The method according to claim 24, wherein the heart rate is not included in the second physical activity feature set.

* * * * *